(12) United States Patent
Astilla et al.

(10) Patent No.: US 12,161,571 B2
(45) Date of Patent: *Dec. 10, 2024

(54) APPARATUS AND METHOD FOR PROTECTING POST-AMPUTATION RESIDUUM

(71) Applicant: Limbguard, LLC, Durham, NC (US)

(72) Inventors: Michael Joseph Astilla, Durham, NC (US); Laura Brewer Riedel, Durham, NC (US)

(73) Assignee: Limbguard, LLC, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/945,737

(22) Filed: Sep. 15, 2022

(65) Prior Publication Data

US 2024/0091031 A1 Mar. 21, 2024

(51) Int. Cl.
*A61F 2/78* (2006.01)

(52) U.S. Cl.
CPC ........ *A61F 2/78* (2013.01); *A61F 2002/7837* (2013.01)

(58) Field of Classification Search
CPC .. A61F 2/78; A61F 2002/7806; A61F 2/7812; A61F 2002/7837
See application file for complete search history.

(56) References Cited

U.S. PATENT DOCUMENTS

| | | | |
|---|---|---|---|
| 3,138,156 A | | 6/1964 | Crowell et al. |
| 3,306,288 A | * | 2/1967 | Rosenfield ............ A61F 13/104 602/76 |
| 3,601,819 A | * | 8/1971 | Herrmann ................. A61F 2/80 623/33 |
| 3,732,578 A | | 5/1973 | Pollack |
| 3,922,727 A | * | 12/1975 | Bianco .................. A61F 2/7812 623/24 |
| 4,840,635 A | | 6/1989 | Smith et al. |
| 5,211,667 A | | 5/1993 | Danforth |
| 5,326,351 A | * | 7/1994 | Sarazin ..................... A61F 2/80 223/111 |

(Continued)

FOREIGN PATENT DOCUMENTS

DE 4321182 12/1994

OTHER PUBLICATIONS

Horton's Orthotic and Prosthetics , How to Use and Maintain Your Prosthetic Shrinker, 1 page, 2018, https://www.youtube.com/watch?v=y2EHCn14bWA.*

*Primary Examiner* — Bruce E Snow
(74) *Attorney, Agent, or Firm* — Taylor English Duma LLP

(57) ABSTRACT

An apparatus for protecting a post-amputation residuum comprises a shell defining a hollow interior cavity adapted for receiving and covering a distal portion of the residuum. The shell has an opening into the cavity at the distal end. A proximal portion of a compression sleeve is adapted to be disposed over at least a portion of the residuum. A free distal portion of the sleeve is configured to extend through the opening in the shell. The sleeve everts upon application of a longitudinal force to the distal portion of the sleeve in a proximal direction for folding over and covering the shell. The distal portion of the sleeve extends proximally of the shell to a position at least partially along the proximal portion of the sleeve for compressing the shell inwardly toward the residuum.

16 Claims, 15 Drawing Sheets

(56) References Cited

U.S. PATENT DOCUMENTS

| | | | | |
|---|---|---|---|---|
| 5,571,209 A * | 11/1996 | Brown, Sr. | ............... | A61F 2/80 623/36 |
| 5,653,766 A * | 8/1997 | Naser | ........................ | A61F 2/80 623/32 |
| 5,888,231 A | 3/1999 | Sandvig et al. | | |
| 7,363,778 B2 | 4/2008 | Pickering et al. | | |
| 8,523,951 B2 | 9/2013 | Kania | | |
| 8,679,193 B2 | 3/2014 | Astilla et al. | | |
| 10,376,390 B1 | 8/2019 | Johnson | | |
| 2018/0185175 A1* | 7/2018 | Whiteside | ................. | A61F 2/78 |
| 2021/0113385 A1 | 4/2021 | Astilla et al. | | |
| 2024/0091069 A1 | 3/2024 | Astilla et al. | | |

* cited by examiner

APPARATUS AND METHOD FOR PROTECTING POST-AMPUTATION RESIDUUM

BACKGROUND

An apparatus and method are described for protecting a post-amputation residuum.

Following amputation of a limb, or a portion of a limb, edema often occurs in the body region of the amputation causing volume fluctuations in the post-amputation residuum. It is important to stabilize the post-amputation residuum by applying compression to the residuum. Compression may be provided by placing the residuum in a splint or a compression sock. When a sock is used, a portion of the sock is slipped over the residuum leaving a free end. A ring receives the free end and the ring is advanced proximally along the sock until it contacts the distal end of the residuum. The free distal end of the sock is then folded over itself toward the proximal end of the sock for providing a compressive double layer of the sock over the residuum. The level of compression of the sock can be adjusted by moving the ring along the sock.

A dedicated post-amputation residuum protection device is available for minimizing swelling and protecting the residuum. One such device is described and shown in U.S. Pat. No. 8,679,193, the contents of which are hereby incorporated by reference in their entirety. The patented residuum protection device may be used after amputation of a portion of a leg and includes a posterior shell, a pre-tibial shell, optional enclosure panels, and a circular pad. The pre-tibial shell is flexible and movable within the posterior shell for accommodating fluctuations in volume of the residuum. The residuum protection device thus stabilizes an amputation residuum while accommodating fluctuations in the volume and the diameter of the residuum.

There is a need for an improved apparatus and method for protecting a post-amputation residuum. The improved apparatus and method should effectively protect the residuum while accommodating variations in volume of the residuum.

SUMMARY

An apparatus is provided for protecting a post-amputation residuum having a distal end. The amputation residuum protection apparatus comprises a shell having a longitudinal axis extending between an open proximal end and a distal end and defining a hollow interior cavity. The shell has an opening into the cavity at the distal end. The shell is adapted for receiving into the cavity a portion of the residuum including the distal end for covering the portion of the residuum within the shell. A compression sleeve has a proximal portion and a distal portion. The proximal portion is adapted to be disposed over at least a portion of the residuum, and the free distal portion of the sleeve is configured to extend through the opening in the distal end of the shell. The sleeve everts upon application of a longitudinal force to the distal portion of the sleeve in a proximal direction for folding over and covering the shell. The distal portion of the everted sleeve extends proximally of the shell to a position at least partially along the proximal portion of the sleeve for compressing the shell inwardly toward the residuum.

A method is provided for post-amputation protection of a residuum having a distal end. The post-amputation residuum protection method comprises providing a shell having a longitudinal axis extending between an open proximal end and a distal end and defining a hollow interior cavity. The shell has an opening into the cavity at the distal end and is adapted for receiving into the cavity a portion of the residuum including the distal end for covering the portion of the residuum within the shell. A tubular compression sleeve having a proximal portion and a distal portion is provide. The proximal portion of the sleeve is disposed over at least a distal portion of the residuum with the free distal portion of the sleeve extending through the opening in the shell. The final step is everting the sleeve upon application of a longitudinal force to the distal portion of the sleeve in a proximal direction for folding over and covering the shell and extending the distal portion of the sleeve proximally of the shell to a position at least partially along the residuum for compressing the shell inwardly toward the residuum.

An apparatus is also provided for protecting a post-amputation residuum having a distal end. The amputation residuum protection apparatus comprises an elongated posterior shell having a longitudinal axis and defining a hollow interior closed at a distal end. The posterior shell having a longitudinal opening extending from a proximal end and adapted to receive the residuum into the hollow interior. A pre-tibial shell has a longitudinal axis and is substantially arcuate in a cross-section taken transverse to the longitudinal axis. The pre-tibial shell is adapted to be positioned adjacent to the residuum and configured to cover at least a portion of the opening of the posterior shell. A distal a shell has a longitudinal axis extending between a proximal end and a distal end and defines a hollow interior cavity. The distal shell has an opening into the cavity at the distal end. The distal shell is configured for receiving into the cavity a distal portion of the combined posterior shell and the pre-tibial shell. A compression sleeve has a proximal portion and a distal portion, the proximal portion adapted to be disposed over at least a portion of the combined posterior shell and the pre-tibial shell. The free distal portion of the sleeve is configured to extend through the opening such that the sleeve everts upon application of a longitudinal force to the distal portion of the sleeve in a proximal direction for folding over and surrounding the shell and a portion of the residuum protection device. The distal portion of the sleeve extends proximally of the shell to a position at least partially along the proximal portion of the residuum protection for compressing the shell inwardly toward the residuum protection device conforming to the outside of the combined shells.

A method is provided for post-amputation protection of a residuum having a distal end. The protection method comprises the steps of providing an elongated posterior shell having a longitudinal axis and defining a hollow interior closed at a distal end, the shell having a longitudinal opening extending from a proximal end and adapted to receive a residuum into the interior of the shell. A residuum is positioned in the interior of the shell via the opening. A second shell is provided and adapted to be positioned adjacent to the residuum, the second shell configured to cover at least a portion of the opening. The second shell is positioned to fit over at least a portion of the residuum exposed through the opening in the shell, wherein at least a portion of an edge of the first shell defining the opening partially overlaps the second shell. A third shell is provided having a longitudinal axis extending between a proximal end and a distal end and defining a hollow interior cavity. The third shell has an opening into the cavity at the distal end and is adapted for receiving into the cavity a portion of the combined posterior shell and the second shell including the distal end for covering the portion of the posterior shell and the second shell within the third shell. A compression sleeve is provided having a proximal portion and a distal portion. The proximal portion of the sleeve is positioned over at least a portion of the combined posterior shell and the second shell, and the free distal portion of the sleeve extends through the opening. The sleeve is everted upon application of a longitudinal force to the distal portion of the sleeve in a proximal direction for folding over and covering the third shell and extending the distal portion of the sleeve proximally of the shell to a position at least partially along the proximal portion of the sleeve for compressing the posterior shell and the second shell inwardly toward the residuum.

In one aspect, the shell for receiving a distal portion of the residuum has a substantially semi-circular shape in a cross-section taken transverse to the longitudinal axis of the shell. The opening in the distal end of said shell is along the central longitudinal axis.

In another aspect, the shell has a plurality of circumferentially spaced longitudinal slits extending from the proximal end partially toward the distal end for allowing the shell to expand or contract. The shell may comprise a soft foam material.

BRIEF DESCRIPTION OF THE DRAWINGS

For a more complete understanding of the post-amputation residuum protection apparatus and method, reference should now be had to the embodiments shown in the accompanying drawings and described below. In the drawings.

DESCRIPTION

Figure 1:
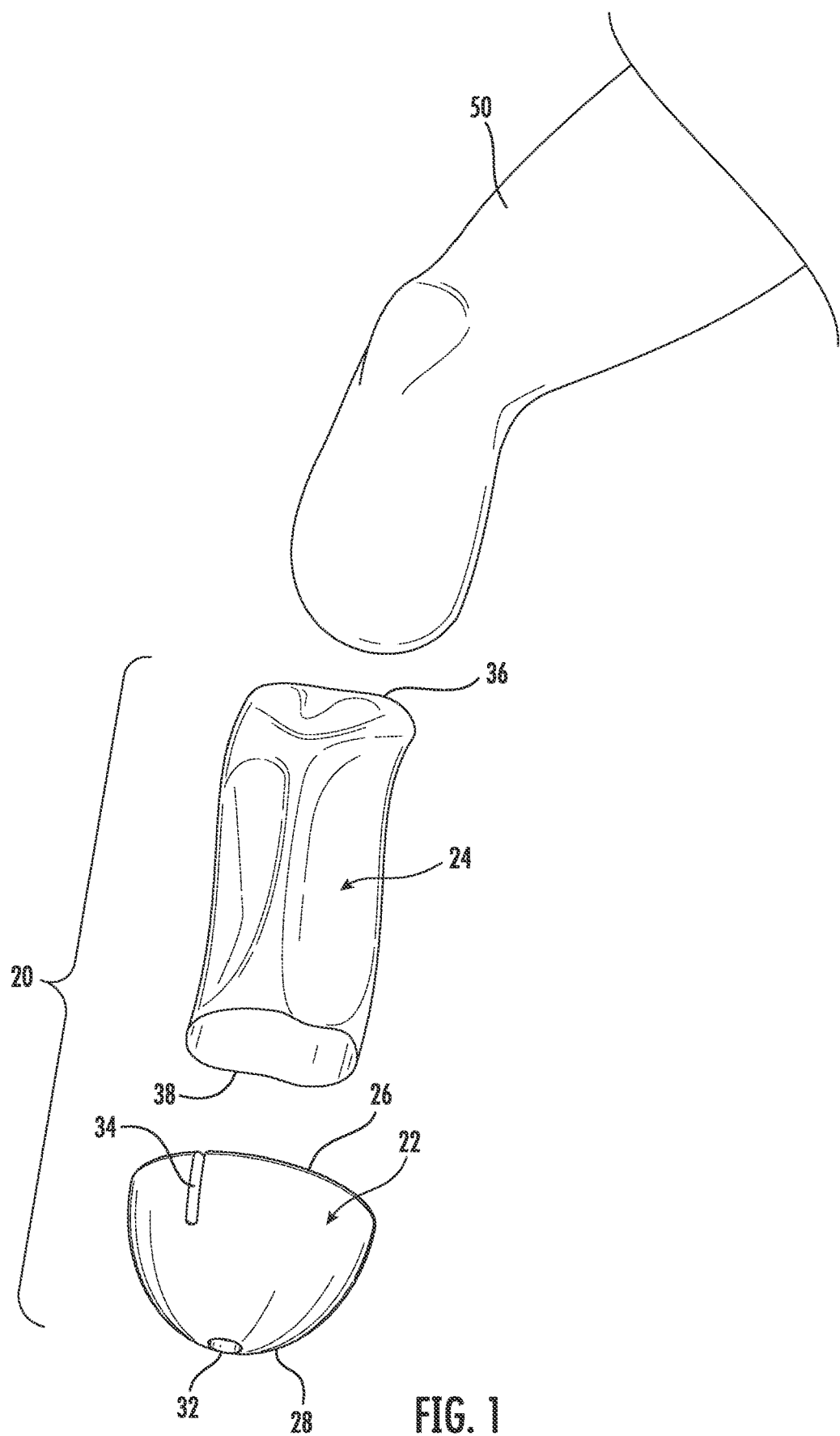
FIG. 1 is an exploded perspective view of an embodiment of an apparatus for protecting a post-amputation residuum.
Figure 2:
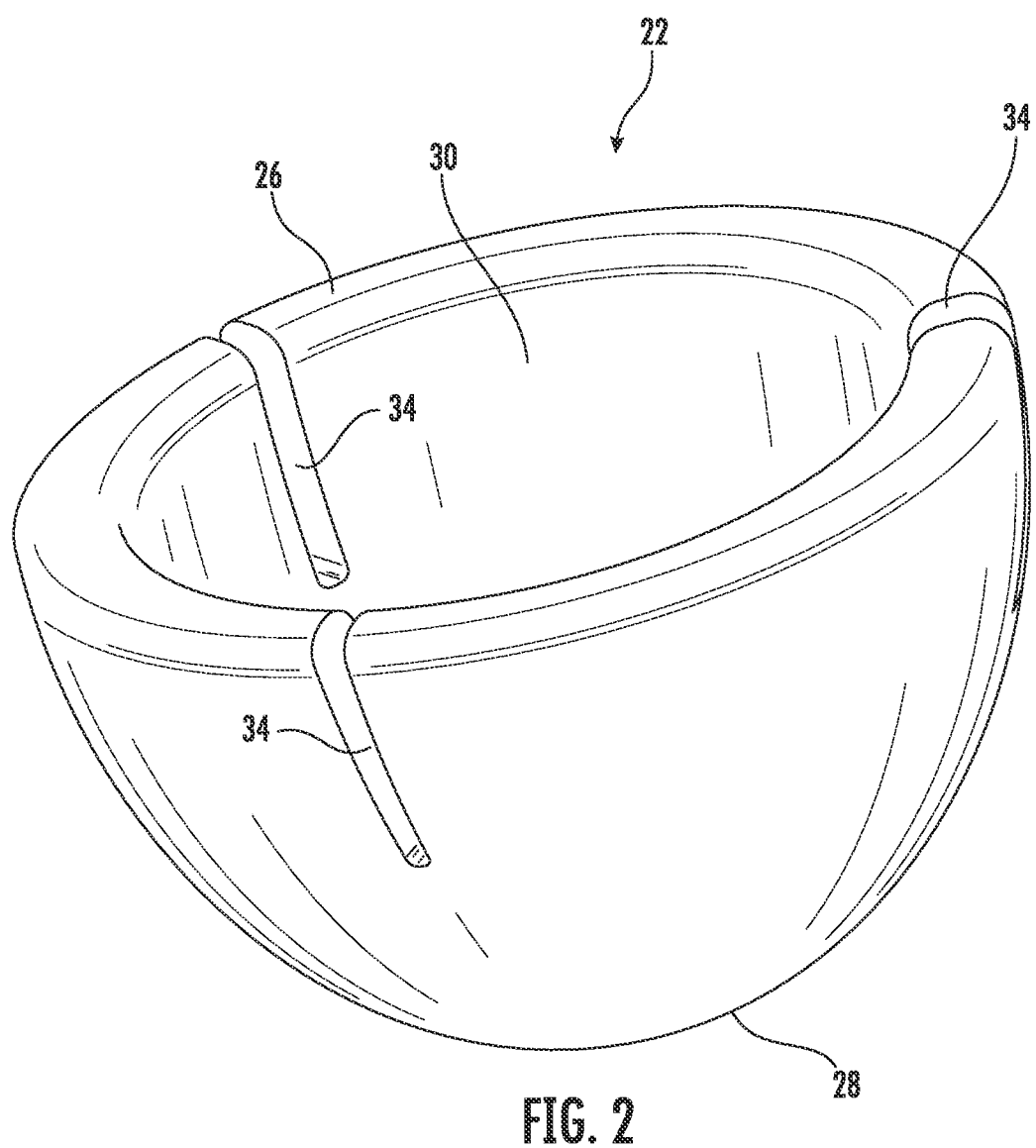
FIG. 2 is a top perspective view of the residuum protection apparatus as shown in FIG. 1.
Figure 3:
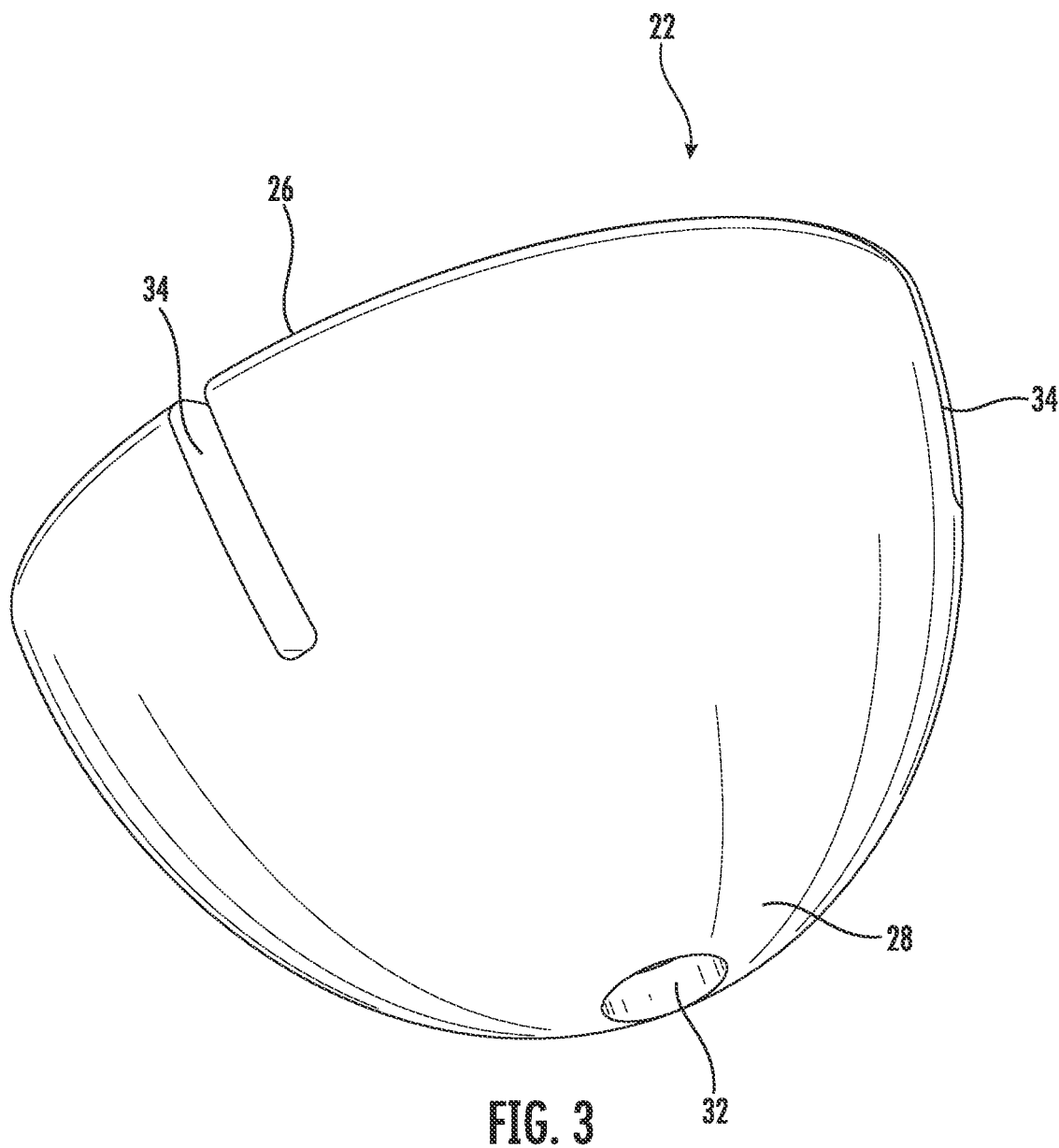
FIG. 3 is a bottom perspective view of the residuum protection apparatus as shown in FIG. 1.
Figure 4:
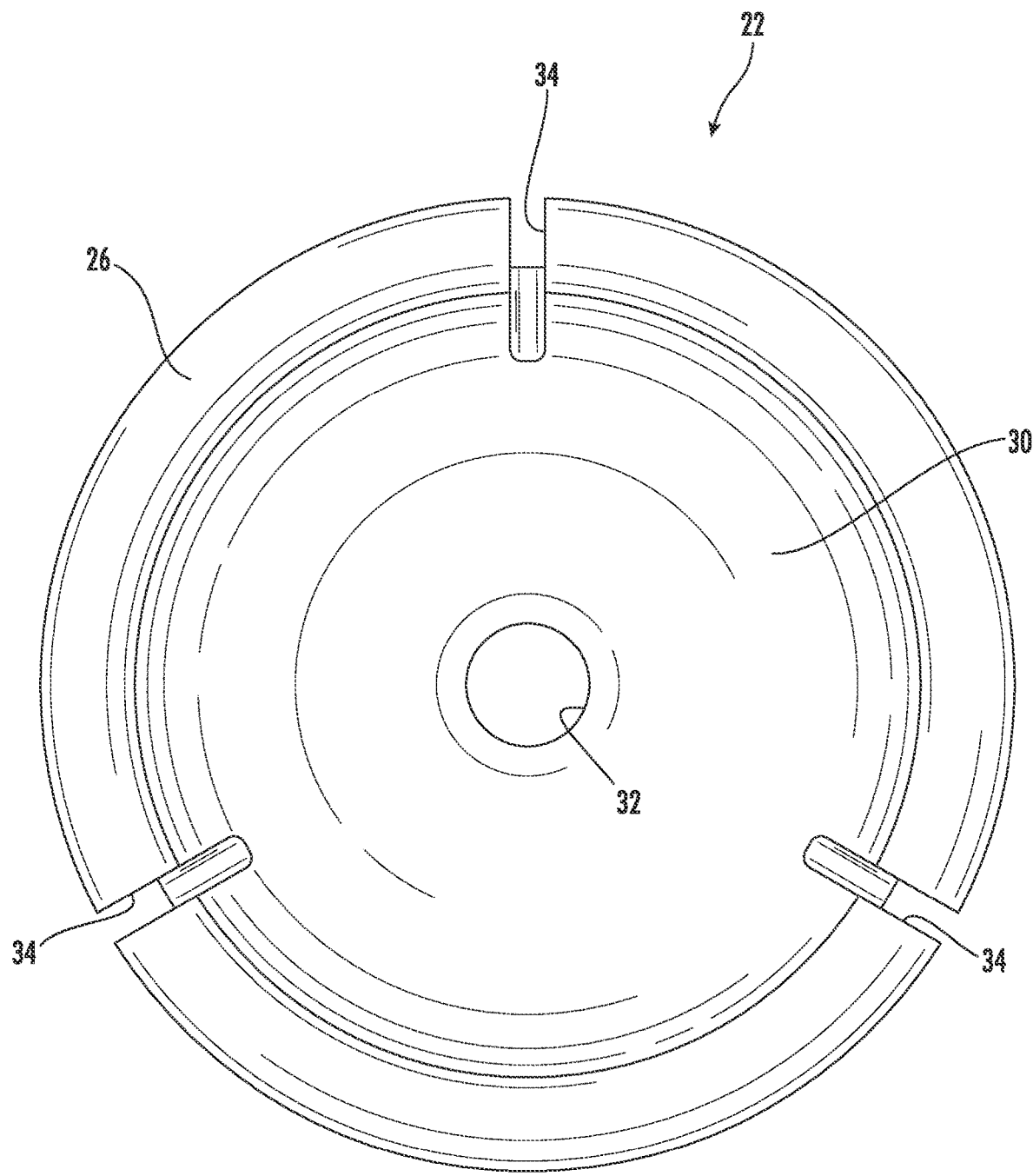
FIG. 4 is a top plan view of the residuum protection apparatus as shown in FIG. 1.
Figure 5:
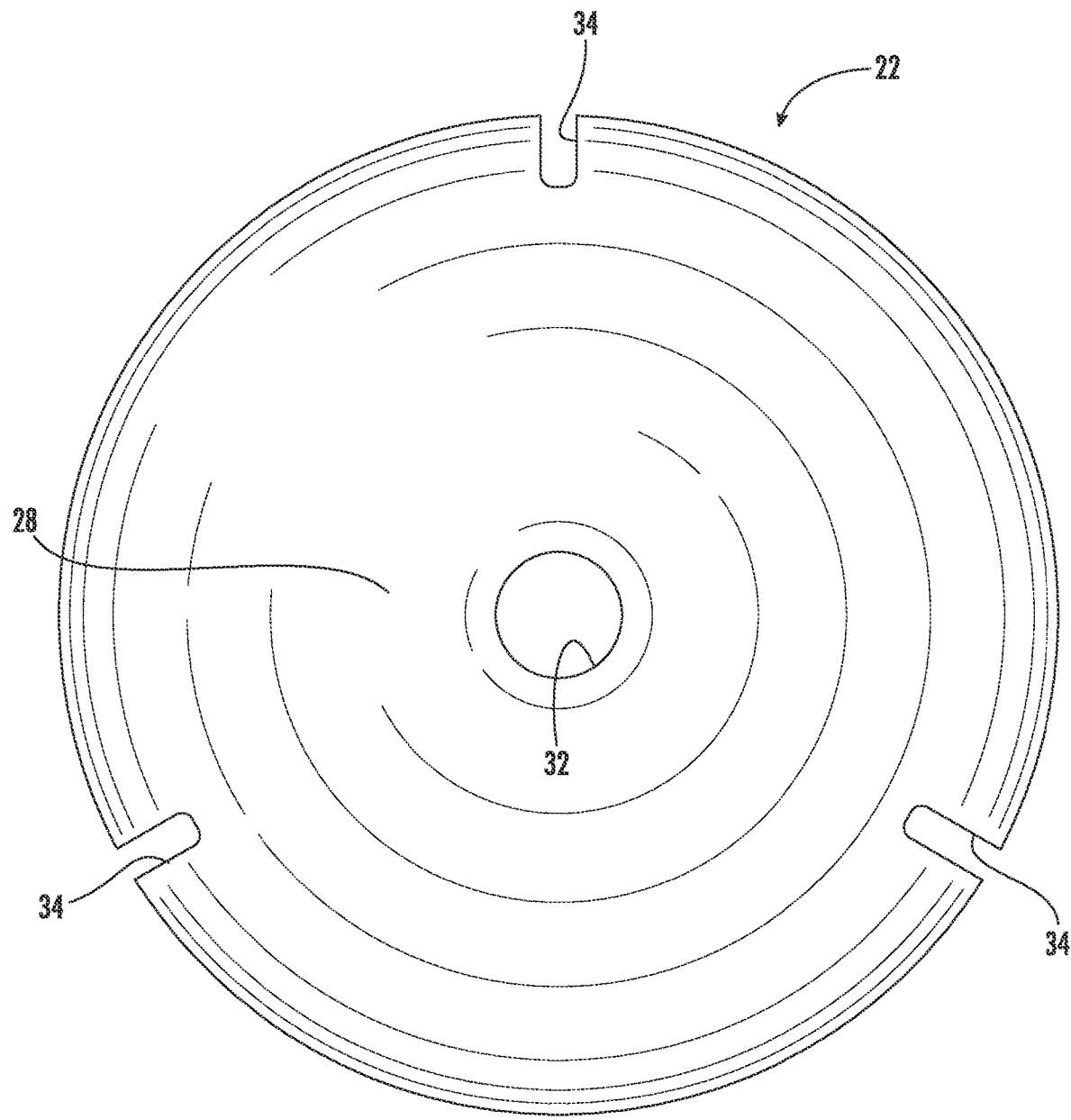
FIG. 5 is a bottom plan view of the residuum protection apparatus as shown in FIG. 1.
Figure 6:
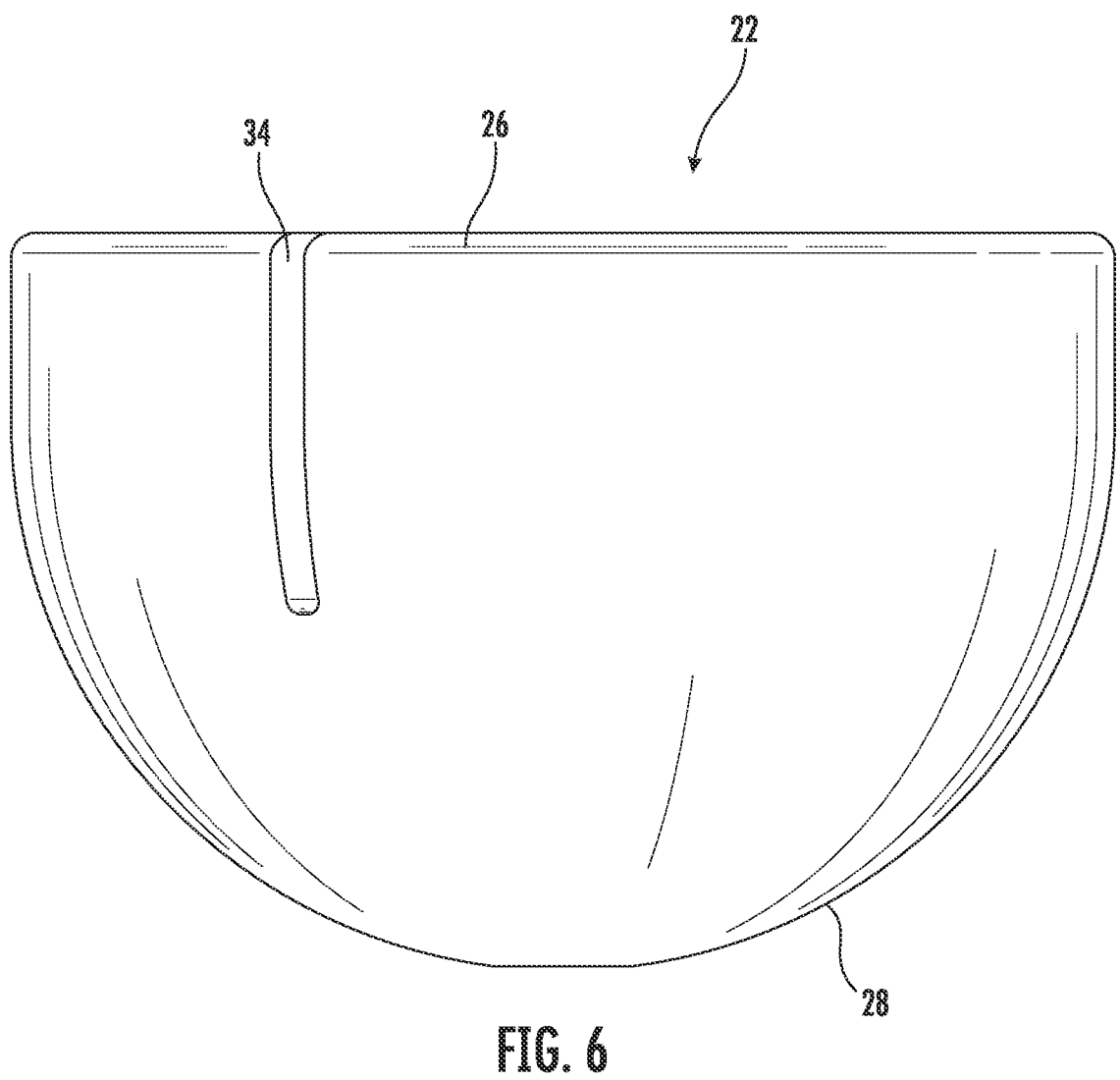
FIG. 6 is a side elevation view of the residuum protection apparatus as shown in FIG. 1.
Figure 7:
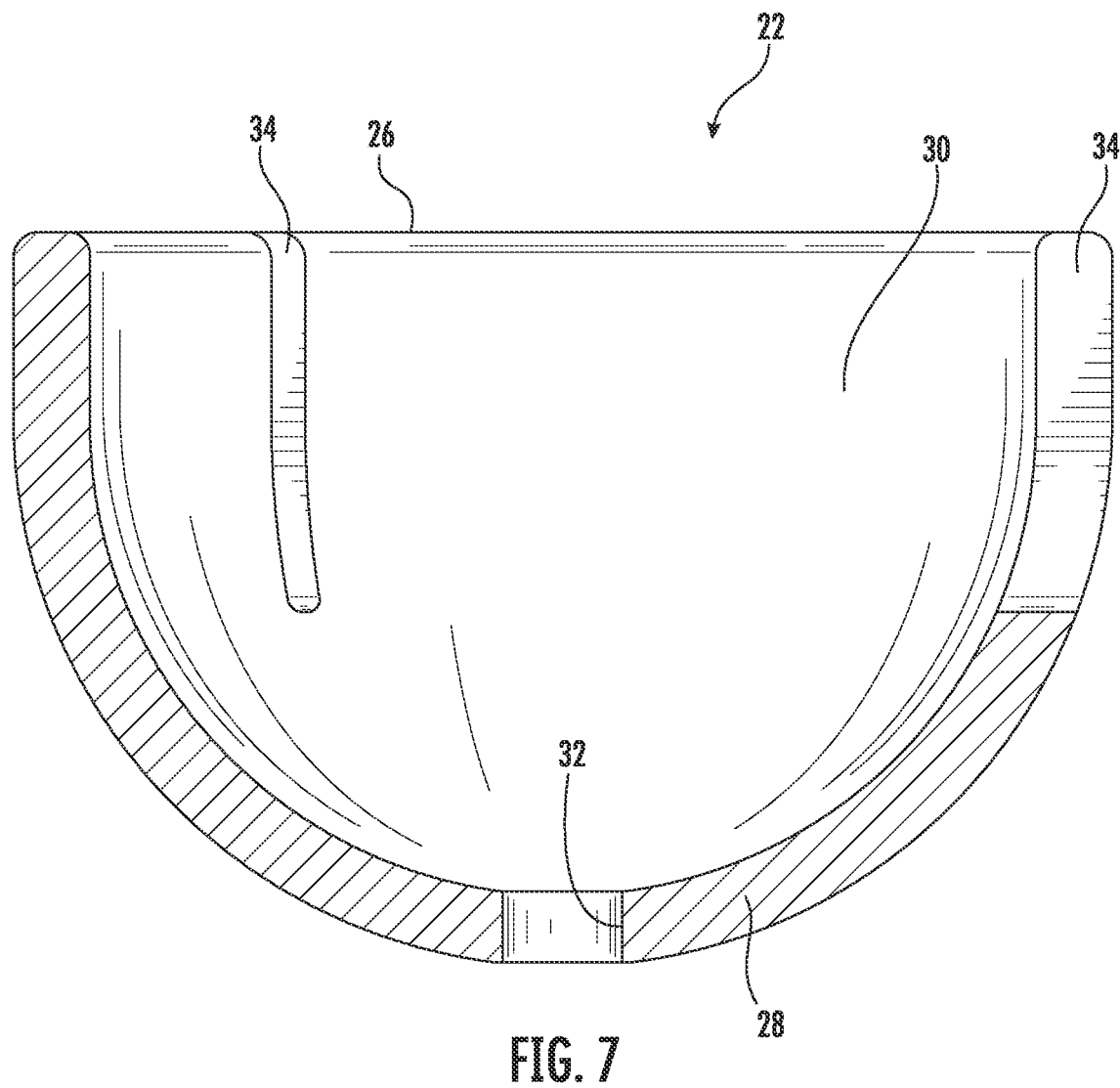
FIG. 7 is a transverse cross-section view of the residuum protection apparatus as shown in FIG. 1 taken along line 7-7 of FIG. 4.

Certain terminology is used herein for convenience only and is not to be taken as a limitation on the invention. For example, words such as "upper," "lower," "left," "right," "horizontal," "vertical," "upward," and "downward" merely describe the configuration shown in the FIGS. Indeed, the components may be oriented in any direction and the terminology, therefore, should be understood as encompassing such variations unless specified otherwise. Where possible, any terms expressed in the singular form herein are meant to also include the plural form and vice versa, unless explicitly stated otherwise. Like numbers refer to like elements throughout. Throughout this disclosure, where a process or method is shown or described, the steps of the method may be performed in any order or simultaneously, unless it is clear from the context that one step depends on another being performed first.

The term "residuum" as used herein includes the remaining portion of an amputated body part, such as an amputated limb and, in particular, an arm or a leg. In one application, as described herein, the leg is amputated above the knee. In another application, the leg is amputated below the knee.

It is understood that, although a residuum protection apparatus and method will be described in detail herein with reference to a particular post-amputation residuum protection device as described in U.S. Pat. No. 8,679,193, the protection apparatus and method may be applied to, and find utility with, other residuum devices or with no other devices. As described above, there a number of devices used for post-amputation residuum protection. Therefore, although the present protection apparatus will be described in detail herein as embodied for use with a particular device, it is not intended to be so limited. The present post-amputation residuum protection apparatus and method may be used with other residuum devices. Thus, the protection apparatus has general applicability to any device providing residuum protection wherein improvements in protection and maintenance of the residuum and ease of use are desired.

Referring now to the drawings, wherein like reference numerals designate corresponding or similar elements throughout the several views, an embodiment of an apparatus for protecting a post-amputation residuum is shown in FIGS. 1-7 and generally designated at 20. The protection apparatus 20 comprises a shell 22 and a compressive sleeve 24. The shell 22 has a proximal end portion 26 and a distal end portion 28 that are spaced along a longitudinal axis L of the shell 22. The shell 22 is open at the proximal end thereby defining an open cavity 30 extending longitudinally inwardly from the proximal end portion 28. The shell 22 has a length and a diameter such that cavity 30 is capable of receiving at least a distal portion of a residuum. The distal end portion 28 of the shell 22 defines a central axial aperture 32. Circumferentially spaced longitudinal slits 34 extend longitudinally from the proximal end 26 and partially along the length of the shell 22. The slits 34 allow the diameter of the shell 22 to expand or contact to fit the variable volume of the post-amputation residuum. The shell 22 may have any thickness and the thickness may vary along the length of the shell. For example, in some embodiments, the proximal end portion 26 of the shell 22 may have a greater thickness than the distal end portion 28.

The shell 22 is generally bowl-shaped as in the embodiment shown in the drawings in order to comfortably accommodate the distal end of a residuum, such as a thigh or the thigh and knee of a trans-tibial residuum following amputation of the leg above or below the knee, respectively.

In some embodiments, the shell 22 is formed from a semi-rigid polymer material. Suitable semi-rigid polymer materials include thermoplastics; polyolefins; plastics; ethylene vinyl acetate, polypropylene, polyethylene, polyethylene terephthalate, styrene, vinyl acetate, acrylonitrile, polyvinyl chloride, polyamide, silicone, rubber, and carbohydrates polymers or copolymers; cross-linked polymers or copolymers; and combinations thereof. The shell 22, in some embodiments, is fabricated by thermo-forming the polymer material over a spherical model. In other embodiments, the shell 22 is formed by injection molding. The shell 22 may have any color or opacity. For example, the shell 22 may be clear, slightly opaque, or completely opaque. In the case where the shell 22 is clear or slightly opaque, the position of the shell 22 or the presence of any collecting fluids may be visible from the outside of the shell 22. Similarly, anything positioned on the outside of the shell 22, such as fabric fasteners, may be visible from the inside.

The shell 22 may comprise a compressive foam. In some embodiments, there may be a plurality of foam layers. For example, an inner foam layer may be laminated to an outer foam layer. The layers may be laminated using heat, adhesive, or a combination thereof. The laminated foam layers may then be cut to size and thermo-molded to a generally bowl-shaped model. Alternatively, one or more layers of the shell 22 is formed through an injection-molding process.

The compression sleeve 24 comprises an expandable tubular structure that can be formed from any smooth, flexible and compressive biocompatible material. The sleeve 24 is configured in diameter and length to cover the shell and at least a portion of the residuum proximal of the shell. As will be described below, when in position over the shell 22 and on the residuum 50, the sleeve 24 is doubled over on itself such that the amount of material used to make the sleeve will be at least double the length desired to cover the shell and the portion of the residuum.

Figure 8:
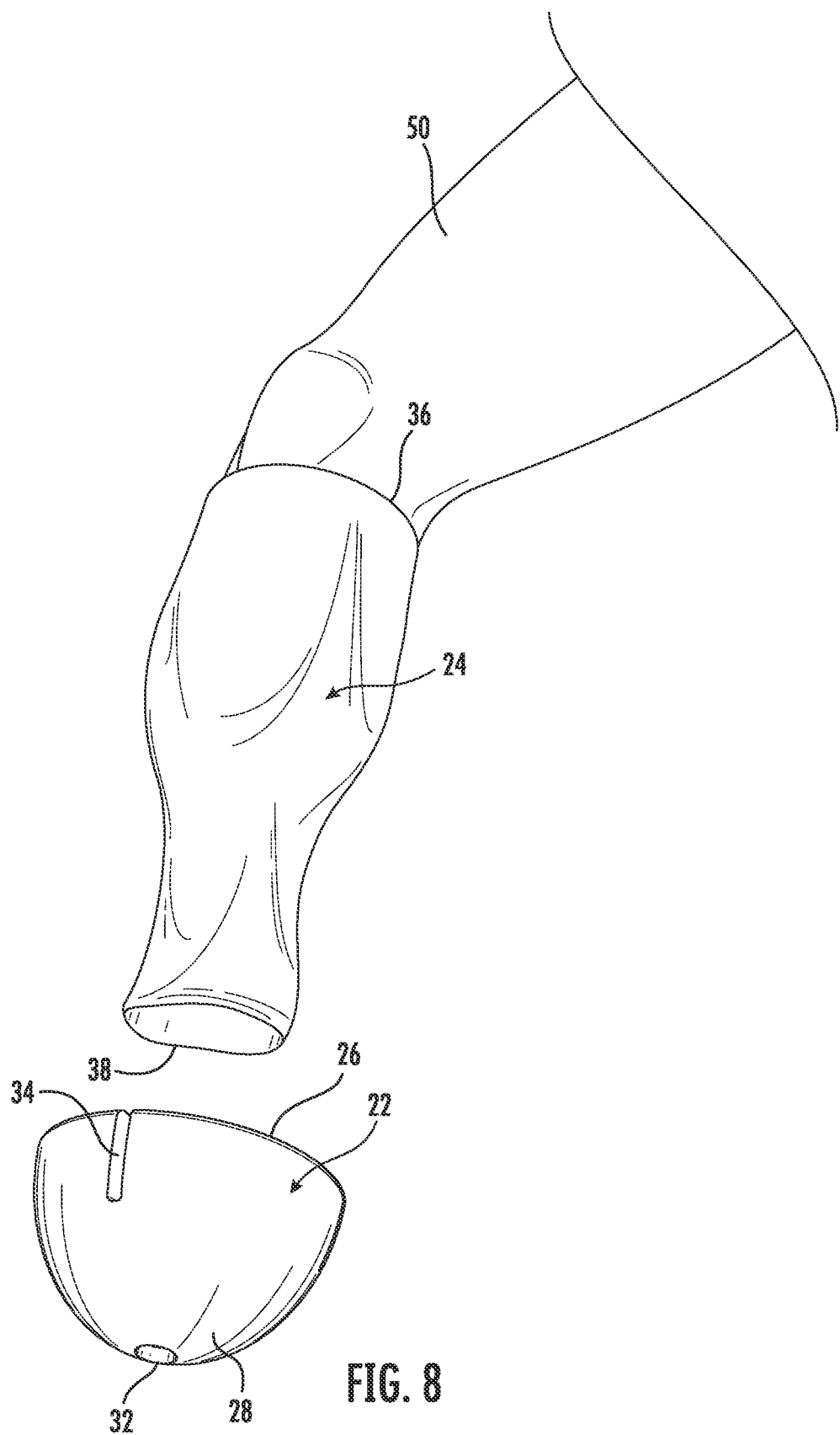
FIG. 8 is a partially exploded perspective view of the residuum protection apparatus as shown in FIG. 8 with a compression sleeve on the residuum.
Figure 9:
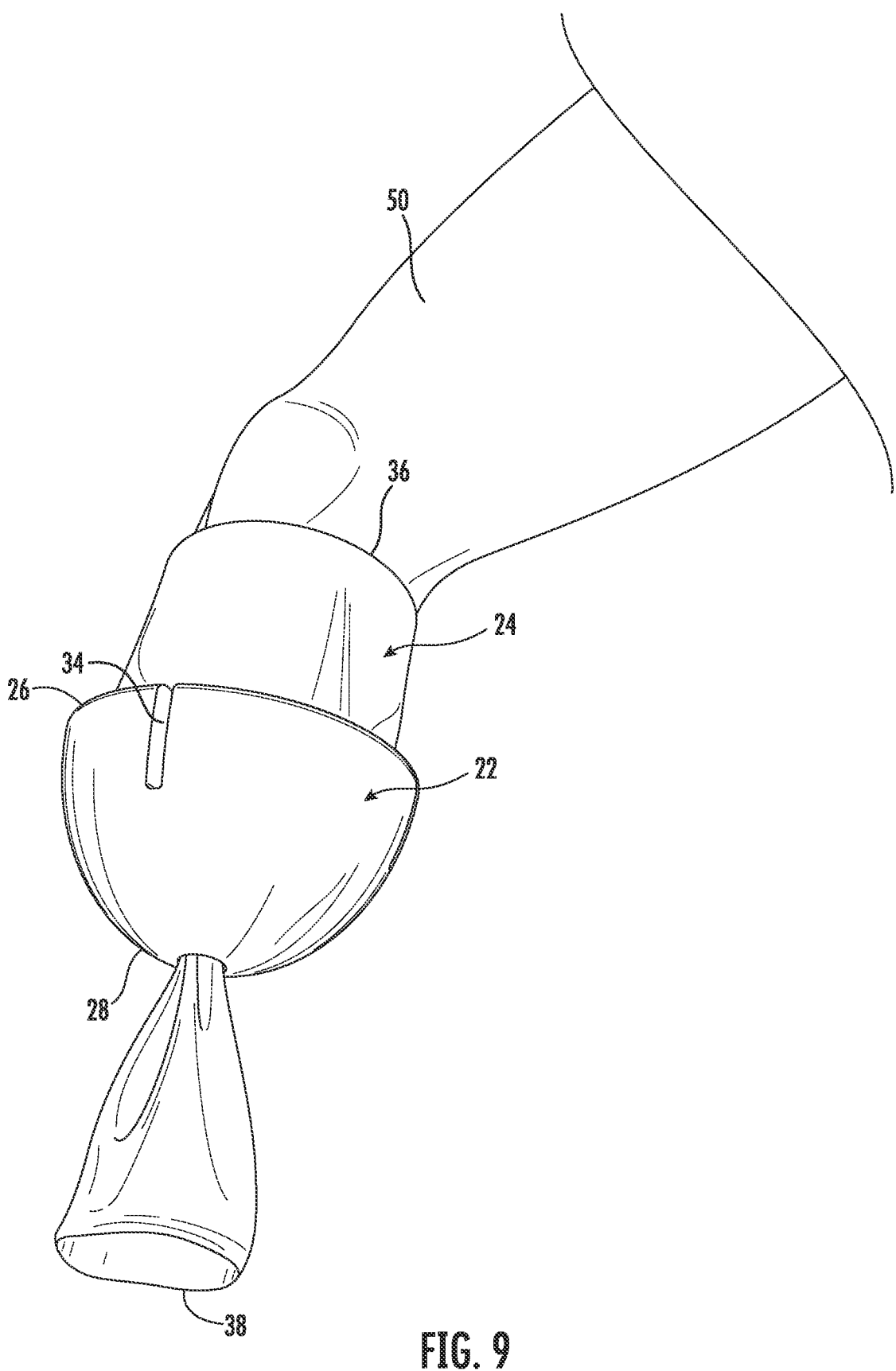
FIG. 9 is a partially exploded perspective view of the residuum protection apparatus as shown in FIG. 8 with a shell on the residuum and receiving a distal portion of the sleeve.
Figure 10:
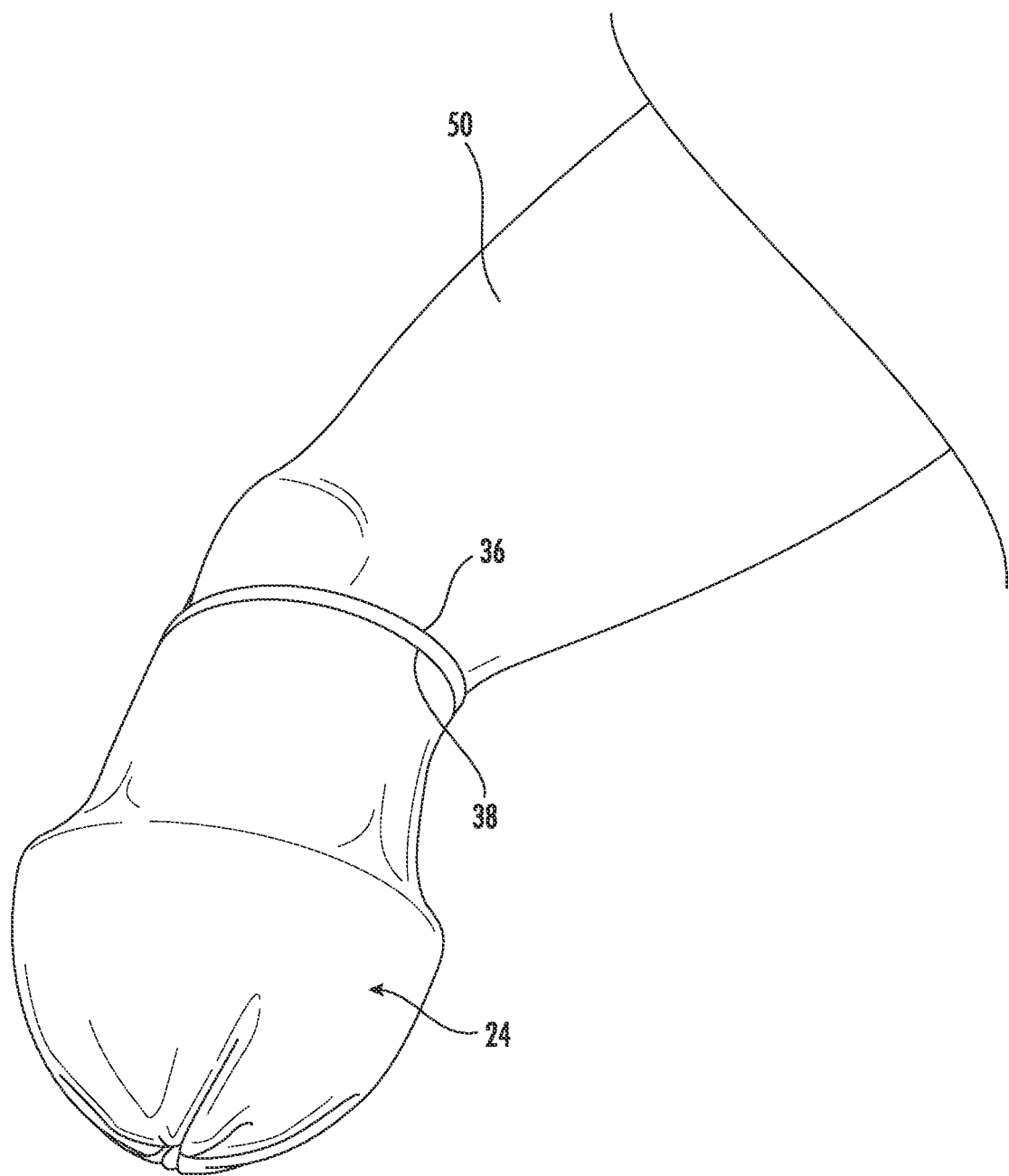
FIG. 10 is a perspective view of the residuum protection apparatus as shown in FIG. 1 in use on a post-amputation residuum of a leg.
Figure 11:
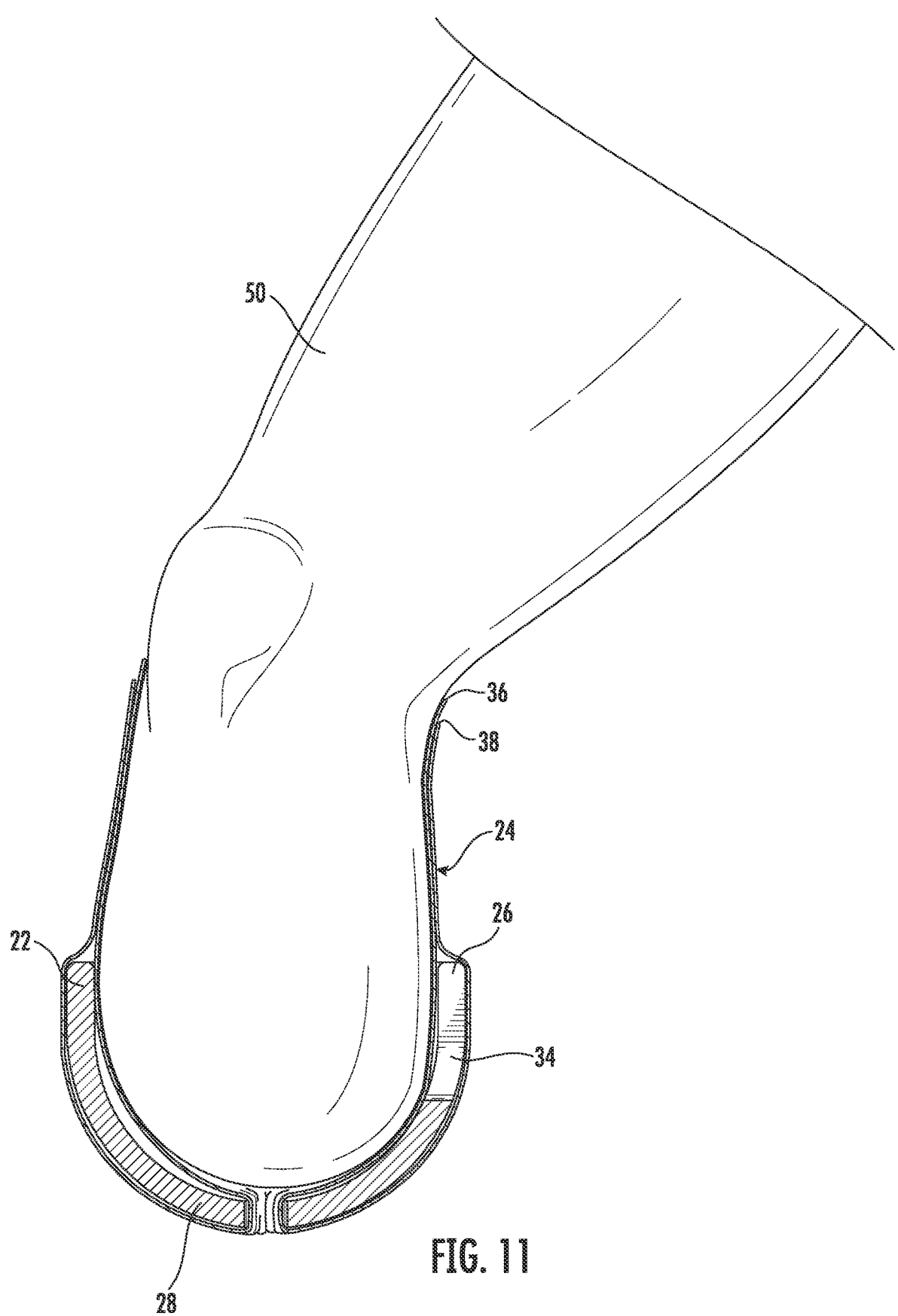
FIG. 11 is an elevation view of a longitudinal cross-section of the residuum protection apparatus as shown in FIG. 10 in use on a post-amputation residuum of a leg.

In use, the protection apparatus 20 may be applied to the post-amputation residuum as shown in FIGS. 8-10. First, the sleeve 24 is pulled onto the residuum 50 and at least partially along the length of the residuum (FIG. 8). Next, the user passes the free distal end 38 of the sleeve 24 through the aperture 32 in the shell 22 (FIG. 9). The shell 22 is advanced proximally along the sleeve 24 and positioned over the distal end portion of the residuum. Upon application of a longitudinal pulling force, the distal end portion 38 of the sleeve 24 is then everted and pulled over the periphery of the shell 22 and a portion of the residuum for enclosing the shell 22 and at least a substantial portion of the residuum proximal of the shell 22 (FIG. 10). The shell 22 remains in a secured position relative to residuum by means of the sleeve 24 conforming to the outside of the residuum. The sleeve 24 is removed by rolling the distal end portion 38 of the sleeve 24 over itself in a distal direction progressively uncovering the shell 22 which can then also be removed from the residuum.

The apparatus 20 is sufficiently flexible to conform to the contour of the shell 22 and the portion of the residuum while accommodating for volume loss or gain secondary to edema within the residuum. The slits 34 further enhance this property by allowing the shell to expand or retract in response to volume and diameter variances in the amputation residuum, thus expanding the possible range of diameters of the shell 22. Moreover, to appropriately accommodate for volume loss secondary to edema reduction within the residuum, the portions of the shell 22 between the slits 34 can overlap one another. This arrangement allows the shell 22 to contract to diameters less than its resting state.

Figure 12A:
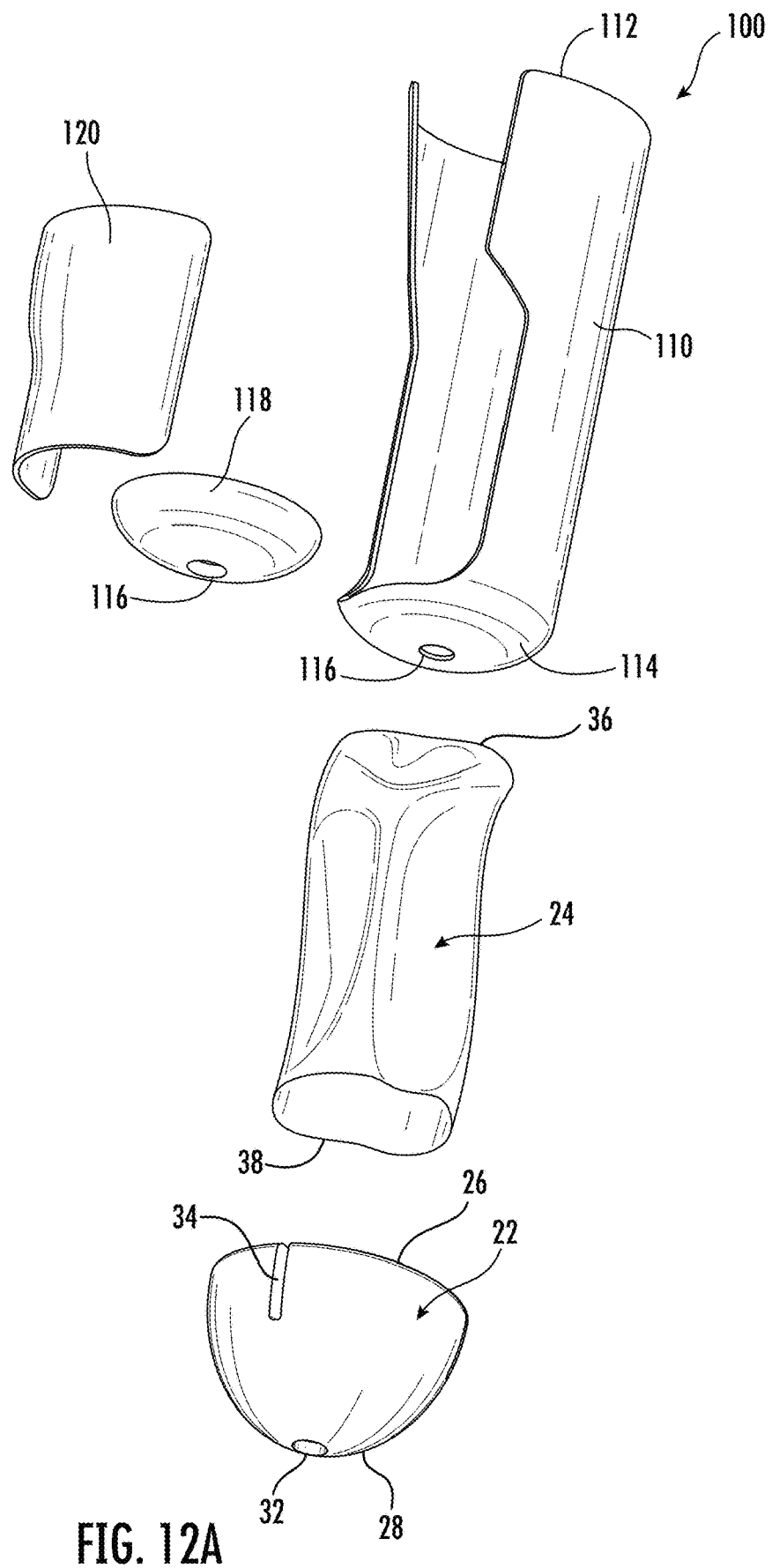
FIG. 12A is an exploded perspective view of the protection apparatus as shown in FIG. 1 with an embodiment of another post-amputation residuum protection device.
Figure 12B:
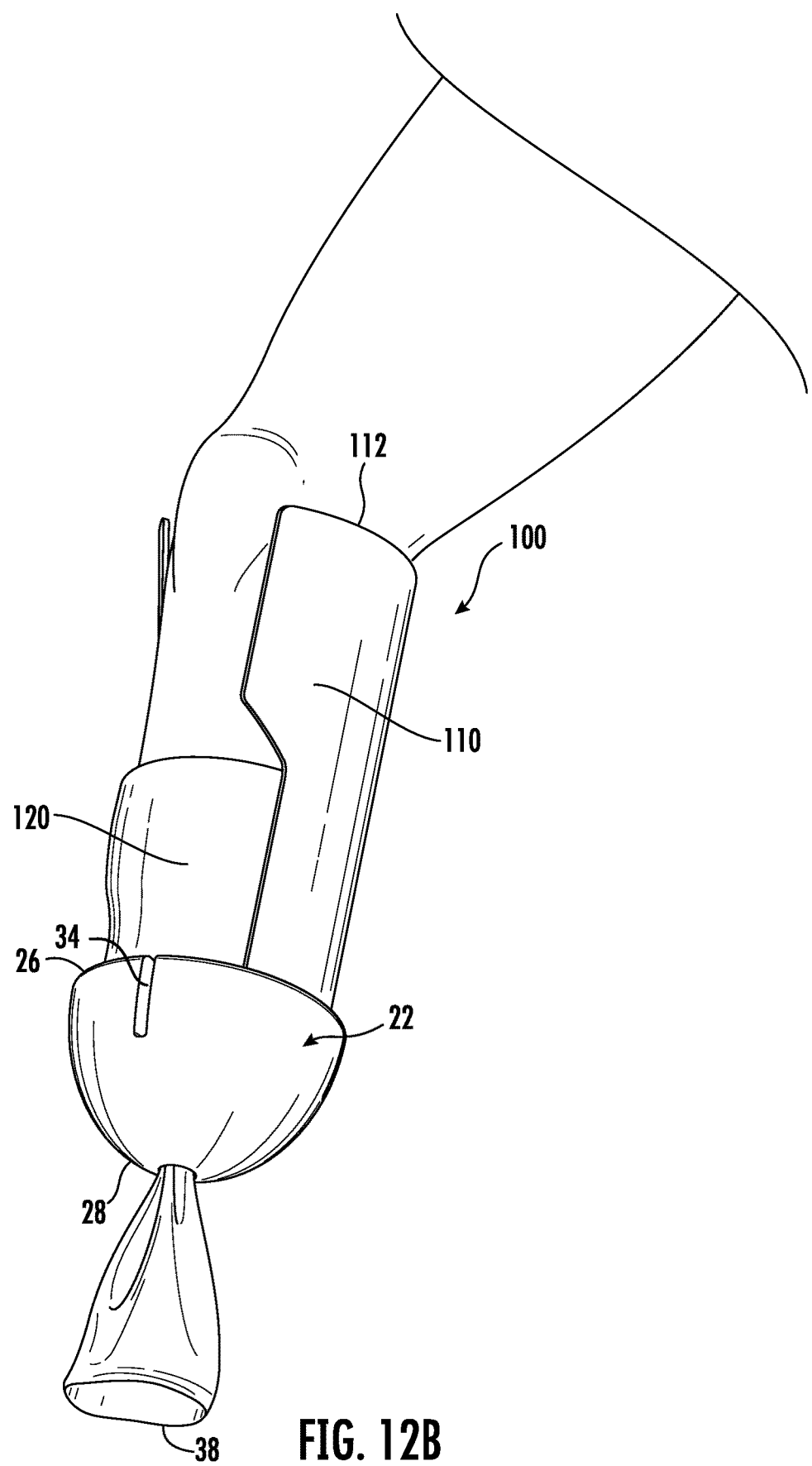
FIG. 12B is a perspective view of the protection apparatus as shown in FIG. 1 assembled with the embodiment of the other post-amputation residuum protection device as shown in FIG. 12A in use on a post-amputation residuum of a leg.

In another embodiment shown in FIG. 12A and FIG. 12B, the protection apparatus 20 may be applied to the post-amputation residuum protection device as shown and described in U.S. Pat. No. 8,679,193 and generally designated at 100. The amputation residuum protection device 100 includes a posterior shell 110 and a pre-tibial shell 120. In use, the sleeve 24 is pulled over the residuum as described hereinabove. The posterior shell 110 is then applied to the posterior of a patient's residual limb by positioning at least a portion of the residuum into the hollow interior of the posterior shell 110. In some embodiments, a proximal end portion 112 of the posterior shell 110 extends along at least a portion of the user's thigh and a distal end portion 114 extends along at least a portion of the user's tibia. The relative position of the posterior shell 110 to the residuum is such that the distal end of the residuum is received in the closed distal end portion 114 of the residuum device 100. An opening 116 is provided in the distal end 114 of the posterior shell 110 for passing the free distal end 38 of the sleeve 22. If a pad 118 is used in the distal end of the posterior shell 110, the pad 118 has a corresponding opening. The pre-tibial shell 120 is positioned in the interior of the posterior shell 110 such that the pre-tibial shell 120 contacts the anterior aspect of the post-amputation residuum. The pre-tibial shell 120 is tucked into the posterior shell 110 to appropriately accommodate for volume loss secondary to edema reduction within the residuum.

The user then passes the sleeve 24 through the shell 22. The shell 22 is then advanced proximally along the sleeve 24 and positioned around and partially over the distal end of the device 100 for covering portions of the posterior shell 110 and the pre-tibial shell 112. Next, the sleeve 24 is everted and pulled over the shell 22 and against the residuum protection device 100. The sleeve 24 extends around the shell 22 and around the assembled posterior shell 110 and the pre-tibial shell 120 and around the proximal portion of the residuum protection device 100 at least partially enveloping the apparatus. The snug fit of the sleeve 22 provides a compressive resistance to distal migration of the shell 22 and the residuum protection device 100 to ensure proper suspension of the residuum protection device 100 keeping the residuum protection device 100 on the limb.

Figure 13A:
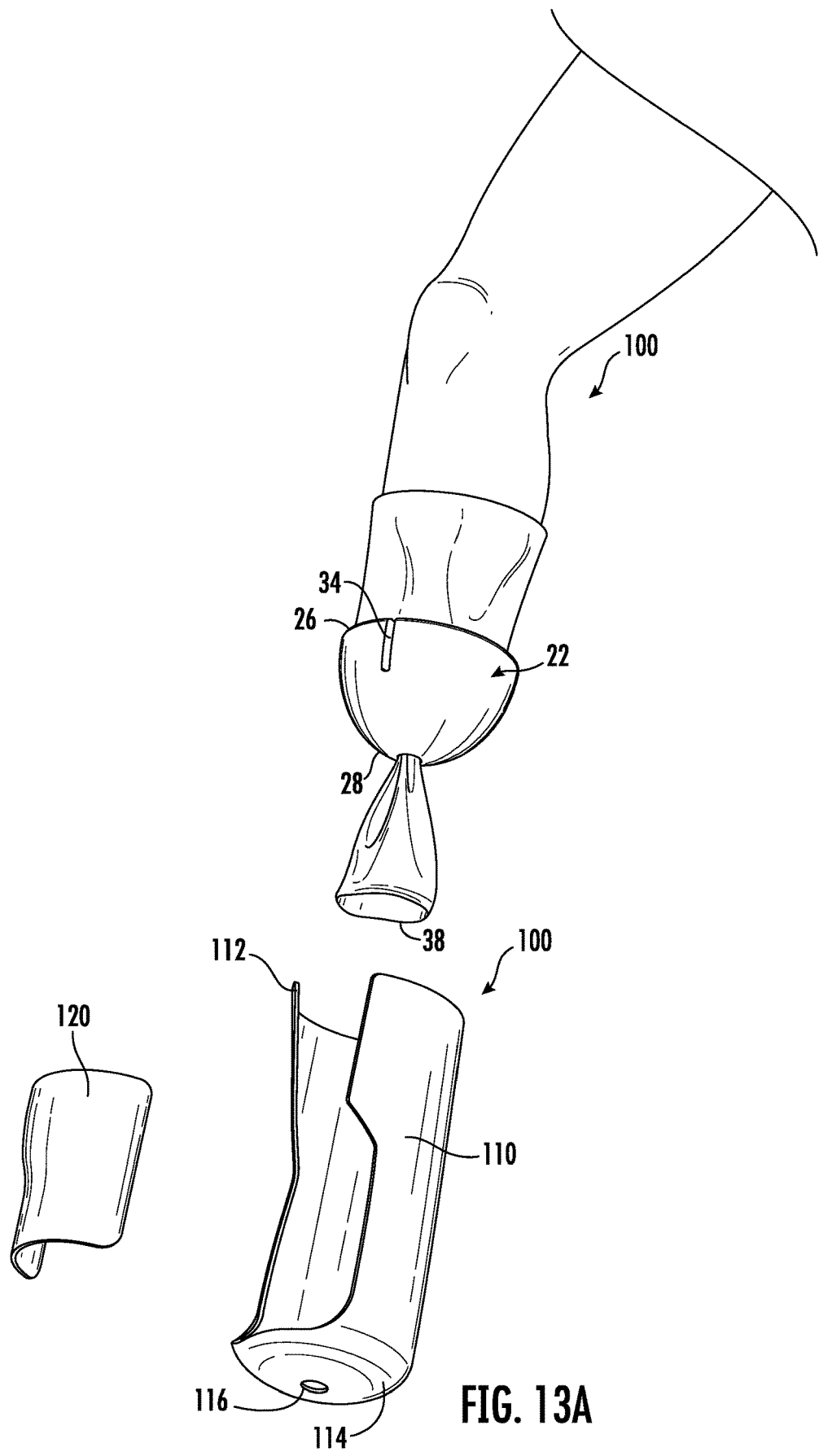
FIG. 13A is an exploded perspective view of the protection apparatus as shown in FIG. 1 with another embodiment of another post-amputation residuum protection device.
Figure 13B:
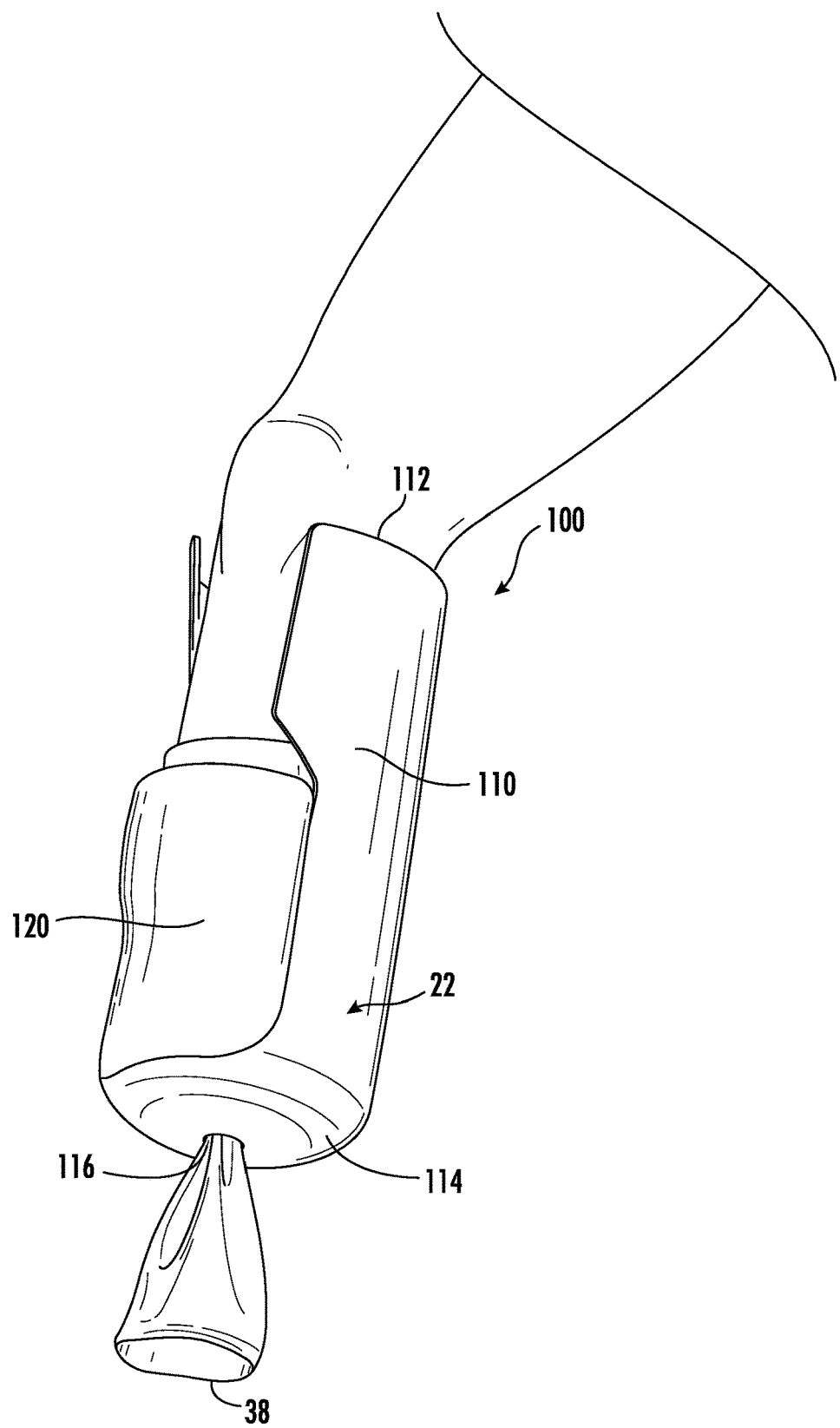
FIG. 13B is a perspective view of the protection apparatus as shown in FIG. 1 assembled with the embodiment of the other post-amputation residuum protection device as shown in FIG. 13A in use on a post-amputation residuum of a leg.

FIG. 13A and FIG. 13B show another embodiment of a method of use of the protection apparatus 20 with the post-amputation residuum protection device 100. In use, the sleeve 24 is pulled over the residuum and the user passes the free distal end 38 of the sleeve 24 through the aperture 32 in the shell 22 as described hereinabove with reference to FIG. 9 (FIG. 13A). The posterior shell 110, the closed distal end of which is enlarged to accommodate the shell 22, is then applied to the posterior of a patient's residual limb by positioning the shell 22 and at least a portion of the residuum into the hollow interior of the posterior shell 110. The free distal end 38 of the sleeve 22 passes through the opening 116 provided in the distal end 114 of the posterior shell 110. The pre-tibial shell 120 may optionally be positioned in the interior of the posterior shell 110 such that the pre-tibial shell 120 contacts the anterior aspect of the post-amputation residuum. The pre-tibial shell 120 is tucked into the posterior shell 110 to appropriately accommodate for volume loss secondary to edema reduction within the residuum. Next, the sleeve 24 is everted and pulled over the residuum protection device 100. The sleeve 24 extends around the assembled posterior shell 110, the inner shell 22 and, if used, the pre-tibial shell 120, and around the proximal portion of the residuum protection device 100 at least partially enveloping the apparatus.

In some embodiments, a kit is provided. The kit comprises one or more residuum protection devices, including one or more of the shell 22 or the sleeve 24. In other embodiments, the kit comprises packaging, a container, instructions, labels, and the like.

The post-amputation residuum protection apparatus 20 has many advantages, including efficacy for a patient with a post-amputation residuum, including an above or below-the-knee amputation. The protection apparatus provides a flexible, wrap-around design configured to accommodate the variable size and shape of the residuum and, if used, another post-amputation residuum protection device for providing a secure and comfortable fit. Due to the design and flexibility of the shell 22, the residuum protection apparatus 20 need not be custom fit for individual patients as the configuration fits numerous individuals of differing bone and tissue structures. Moreover, the apparatus 20 accommodates size changes as the residuum anatomy changes due to volume fluctuations resulting in consistent, optimal residuum protection.

Although the protection apparatus and method have been shown and described in considerable detail with respect to only a few exemplary embodiments thereof, it should be understood by those skilled in the art that we do not intend to limit the apparatus and method to the embodiments since various modifications, omissions and additions may be made to the disclosed embodiments without materially departing from the novel teachings and advantages of the protection apparatus, particularly in light of the foregoing teachings. For example, while the protection apparatus and method are shown and described herein for use with a leg, it will be understood that the apparatus may also be used for an arm or other body part. Accordingly, we intend to cover all such modifications, omissions, additions and equivalents as may be included within the spirit and scope of the protection apparatus as defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. An apparatus for protecting a post-amputation residuum having a distal end, the apparatus for protecting the post-amputation residuum comprising:
    a shell having a central longitudinal axis extending between an open proximal end and a distal end and defining a hollow interior cavity, the shell having a plurality of circumferentially spaced longitudinal slits extending from the proximal end partially toward the distal end for allowing the shell to expand or contract, and an opening into the cavity at the distal end, the shell adapted for receiving at the proximal end into the cavity a portion of the residuum including the distal end for covering the portion of the residuum within the shell; and
    a tubular compression sleeve having a proximal portion and a distal portion, the proximal portion of the sleeve adapted to be disposed over at least a portion of the residuum, and the distal portion of the sleeve configured to extend through the opening in the distal end of the shell such that the sleeve everts upon application of a longitudinal force to the distal portion of the sleeve in a proximal direction for folding over and covering the shell, the distal portion of the sleeve extending proximally of the shell to a position at least partially along the proximal portion of the sleeve for compressing the shell inwardly toward the residuum.

2. The post-amputation residuum protection apparatus as recited in claim 1, wherein the shell has a substantially semi-circular shape in a cross-section taken transverse to the longitudinal axis of the shell.

3. The post-amputation residuum protection apparatus as recited in claim 1, wherein the opening in the distal end of the shell is along the central longitudinal axis.

4. The post-amputation residuum protection apparatus as recited in claim 1, wherein the shell comprises a soft foam material.

5. A method for post-amputation protection of a residuum having a distal end, the method for post-amputation protection of the residuum comprising the steps of:
    providing a shell having a longitudinal axis extending between an open proximal end and a distal end and defining a hollow interior cavity, the shell having a plurality of circumferentially spaced longitudinal slits extending from the proximal end partially toward the distal end for allowing the shell to expand or contract, and an opening into the cavity at the distal end and adapted for receiving into the cavity a portion of the residuum including the distal end for covering the portion of the residuum within the shell;
    providing a tubular compression sleeve having a proximal portion and a distal portion;
    disposing the proximal portion of the sleeve over at least a distal portion of the residuum;
    extending the free distal portion of the sleeve through the opening in the shell; and
    everting the sleeve upon application of a longitudinal force to the distal portion of the sleeve in a proximal direction for folding over and covering the shell and extending the distal portion of the sleeve proximally of the shell to a position at least partially along the residuum for compressing the shell inwardly toward the residuum.

6. The post-amputation residuum protection method as recited in claim 5, wherein the shell has a substantially semi-circular shape in a cross-section taken transverse to the longitudinal axis of the shell.

7. The post-amputation residuum protection method as recited in claim 5, wherein the opening in the distal end of the shell is along the central longitudinal axis.

8. The post-amputation residuum protection method as recited in claim 5, wherein the shell comprises a soft foam material.

9. An apparatus for protecting a post-amputation residuum having a distal end, the apparatus for protecting the post-amputation residuum comprising:
    a residuum protection device including
        an elongated posterior shell having a longitudinal axis and defining a hollow interior and having opening into the interior at a distal end, the posterior shell having a longitudinal opening extending from a proximal end and adapted to receive the residuum into the hollow interior, and a pre-tibial shell having a longitudinal axis and substantially arcuate in a cross-section taken transverse to the longitudinal axis, the pre-tibial shell adapted to be positioned adjacent to the residuum and configured to cover at least a portion of the longitudinal opening of the posterior shell;

a distal shell having a longitudinal axis extending between an open proximal end and a distal end and defining a hollow interior cavity, the distal shell having a plurality of circumferentially spaced longitudinal slits extending from the proximal end partially toward the distal end for allowing the shell to expand or contract, and an opening into the cavity at the distal end, the distal shell configured for receiving at the proximal end into the cavity a distal portion of the assembled posterior shell and the pre-tibial shell for covering the portion of the posterior shell and the pre-tibial shell; and a tubular compression sleeve having a proximal portion and a distal portion, the proximal portion of the sleeve configured to be disposed over at least a portion of the residuum, and the distal portion of the sleeve configured to extend through the opening in the distal end of the posterior shell such that the sleeve everts upon application of a longitudinal force to the distal portion of the sleeve in a proximal direction for folding over and surrounding the distal shell and a portion of the residuum protection device, the distal portion of the sleeve extending proximally of the distal shell to a position at least partially along the proximal portion of the residuum protection device for compressing the distal shell inwardly toward the residuum protection device.

10. The post-amputation residuum protection apparatus as recited in claim 9, wherein the shell has a substantially semi-circular shape in a cross-section taken transverse to the longitudinal axis of the shell.

11. The post-amputation residuum protection apparatus as recited in claim 9, wherein the opening in the distal end of the shell is along the central longitudinal axis.

12. The post-amputation residuum protection apparatus as recited in claim 9, wherein the shell comprises a soft foam material.

13. A method for post-amputation protection of a residuum having a distal end, the method for post-amputation protection of the residuum comprising the steps of:

providing an elongated posterior shell having a longitudinal axis and defining a hollow interior and having an opening into the interior at a distal end, the posterior shell having a longitudinal opening extending from a proximal end and adapted to receive a residuum into the interior of the posterior shell;

positioning a residuum in the interior of the posterior shell via the longitudinal opening;

providing a second shell adapted to be positioned adjacent to the residuum, the second shell configured to cover at least a portion of the longitudinal opening;

positioning the second shell to fit over at least a portion of the residuum exposed through the longitudinal opening in the posterior shell, wherein at least a portion of an edge of the posterior shell defining the opening partially overlaps the second shell;

providing a third shell having a longitudinal axis extending between an open proximal end and a distal end and defining a hollow interior cavity, the third shell having a plurality of circumferentially spaced longitudinal slits extending from the proximal end partially toward the distal end for allowing the third shell to expand or contract, and an opening into the cavity at the distal end, the third shell adapted for receiving into the cavity a portion of the assembled posterior shell and the second shell including the distal end for covering the portion of the posterior shell and the second shell within the third shell;

providing a tubular compression sleeve having a proximal portion and a distal portion;

disposing the proximal portion of the sleeve over at least a distal portion of the assembled posterior shell and the second shell;

extending the free distal portion of the sleeve through the opening in the posterior shell; and everting the sleeve upon application of a longitudinal force to the distal portion of the sleeve in a proximal direction for folding over and covering the third shell and extending the distal portion of the sleeve proximally of the third shell to a position at least partially along the assembled posterior shell and the second shell for compressing the posterior shell and the second shell and the third shell inwardly toward the residuum.

14. The post-amputation residuum protection method as recited in claim 13, wherein the third shell has a substantially semi-circular shape in a cross-section taken transverse to the longitudinal axis of the third shell.

15. The post-amputation residuum protection method as recited in claim 13, wherein the opening in the distal end of the third shell is along the central longitudinal axis.

16. The post-amputation residuum protection method as recited in claim 13, wherein the third shell comprises a soft foam material.

* * * * *